US00RE39240E

(19) United States
(12) Reissued Patent
Olivera et al.

(10) Patent Number: US RE39,240 E
(45) Date of Reissued Patent: Aug. 15, 2006

(54) CONOTOXINS I

(75) Inventors: Baldomero M. Olivera, Salt Lake City, UT (US); Jean E. F. Rivier, La Jolla, CA (US); Lourdes J. Cruz, Salt Lake City, UT (US); Fe Abogadie, Evanston, IL (US); Chris E. Hopkins, Salt Lake City, UT (US); John Dykert, Vista, CA (US); Josep L. Torres, Barcelona (ES)

(73) Assignees: University of Utah Research Foundation, Salt Lake City, UT (US); The Salk Institute for Biological Studies, LaJolla, CA (US)

(21) Appl. No.: 09/469,496

(22) Filed: Dec. 22, 1999

Related U.S. Patent Documents

Reissue of:
(64) Patent No.: 5,700,778
Issued: Dec. 23, 1997
Appl. No.: 08/458,499
Filed: Jun. 2, 1995

U.S. Applications:
(62) Division of application No. 08/084,848, filed on Jun. 29, 1993, now Pat. No. 5,432,155.

(51) Int. Cl.
*C07K 7/08* (2006.01)
*C07K 14/435* (2006.01)

(52) U.S. Cl. ..... 514/12; 530/324; 530/326; 530/325; 514/13; 514/14

(58) Field of Classification Search ..... 530/324, 530/325, 326; 514/857, 12, 13, 14; 424/547
See application file for complete search history.

(56) References Cited

U.S. PATENT DOCUMENTS

| | | | | | |
|---|---|---|---|---|---|
| 4,447,356 | A | * | 5/1984 | Olivera et al. | 530/327 |
| 4,925,664 | A | * | 5/1990 | Jackson et al. | 424/537 |
| 5,089,474 | A | * | 2/1992 | Castro et al. | 514/12 |
| 5,231,011 | A | * | 7/1993 | Hillyard et al. | 435/69.7 |
| 5,270,170 | A | * | 12/1993 | Schatz et al. | 435/7.37 |
| 5,281,693 | A | * | 1/1994 | Jackson et al. | 530/324 |

OTHER PUBLICATIONS

Fainzilber et al. "Mollusc–specific toxins from the venom of Conus textile neovicarius." European journal of biochemistry 202(2): p 589–95, Dec. 1991.*

Fainzilber et al. "Mollusc–specific toxins from the venom of Conus textile neovicarius." Medline Abstract #92104183, Dec. 1991.*

Gray, G.W. (1993) "Multicyclic Cystine Peptides: A New Method for Disulfide Analysis", *Thirteenth American Peptide Symposium*, University of Utah Department of Biology, Abstract Wk5 pp. 1085–1087.

Olivera, B.M. et al. (1991) "Conotoxins", *The Journal of Biological Chemistry*, vol. 266 No. 33: 22067–22070.

Olivera, B.M. et al. (1990) "Diversity of Conus Neuropeptides", *Science,* 249:257–263.

Mena, E.E. et al. (1990) "Conantokin–G: a novel peptide antagonist to the N–methyl–D–aspartic acid (NMDA) receptor", *Neuroscience Letters*, 118:241–244.

Penke, B. et al. (1987) "Solid Phase Synthesis of Peptide Amides on a Polystyrene Support Using Fluorenylemethoxycarbonyl Protecting Groups", Journal of Organic Chemistry 52:1197–1200.

Rivier, J. et al. (1987) "Total Synthesis and Further Characterization of the *y*–Carboxyglutamate–Containing "Sleeper" Peptide from *Conus geographus* Venom", *Biochemistry,* 26:8508–8512.

Olivera, B.M. et al. (1991) "Conus Peptides and Biotechnology", *Neurotox*, 45–55.

Haack, J.A. et al. (1990) "Conantokin–T–A–*y*–Carboxyglutamate Containing Peptide with *N*–Methyl–D–Aspartate Antagonist", *The Journal of Biological Chemistry*, vol. 265 No. 11:6025–6029.

Olivera, B.M. et al. (1985) "Peptide Neurotoxins from Fish–Hunting Cone Snails", *Science*, 230:1338–1343.

Torres, J.L. et al. (1993) "Structure–Activity Studies of Conantokin–G Analogs", *Thirteenth American Peptide Symposium*, Abstract P421, pp. 526–528.

* cited by examiner

*Primary Examiner*—Gabriele Bugaisky
(74) *Attorney, Agent, or Firm*—Rothwell Figg Ernst & Manbeck

(57) ABSTRACT

Substantially pure conotoxins are provided which inhibit synaptic transmissions at the neuromuscular junctions and which are useful both in vivo and in assays because they specifically target particular receptors, such as the acetylcholine receptor, and ion channels. The peptides are of such length that they can be made by chemical synthesis. They also may be made using recombinant DNA techniques, and the DNA encoding such conotoxins having pesticidal properties can be incorporated as plant defense genes into plant species of interest.

22 Claims, No Drawings

CONOTOXINS I

Matter enclosed in heavy brackets [ ] appears in the original patent but forms no part of this reissue specification; matter printed in italics indicates the additions made by reissue.

This is a division of application Ser. No. 08/084,848, filed on Jun. 29, 1993, now U.S. Pat. No. 5,432,155.

This invention was made with Government support under Grant Nos. GM-22737 and AM-26741, awarded by the National Institute of Health. The Government has certain rights in this invention.

This invention relates to relatively short peptides, and more particularly to peptides between about 16 and about 46 residues in length, which are naturally available in minute amounts in the venom of the cone snails and which may include one or more cyclizing disulfide linkages.

BACKGROUND OF THE INVENTION

Mollusks of the genus Conus produce a highly toxic venom which enables them to carry out their unique predatory lifestyle. Prey are immobilized by the venom which is injected by means of a highly specialized venom apparatus, a disposable hollow tooth which functions both in the manner of a harpoon and a hypodermic needle.

Few interactions between organisms are more striking than those between a venomous animal and its eaveaomated victim. Venom may be used as a primary weapon to capture prey or as a defense mechanism. These venoms disrupt essential organ systems in the envenomated animal, and many of these venoms contain molecules directed to receptors and ion channels of neuromuscular systems.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such they are somewhat unusual because peptides in this size range normally equilibrate among many conformations for proteins having a fixed conformation are generally much larger.

The cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used; however, every Conus species uses fundamentally the same basic pattern of envenomation.

The major paralytic peptides is these fish-hunting cone venoms were the first to be identified and characterized. In C. geographus venom, three classes of disulfide-rich peptides were found: the α-conotoxins (which target and block the nicotinic acetylcholine receptors); the μ-conotoxins (which target and block the skeletal muscle $Na^+$ channels); and the Ω-conotoxins (which target and block the presynaptic neuronal $Ca^{2+}$ channels). However, there are multiple homologs in each toxin class; for example, at least five different Ω-conotoxins are present in C. geographus venom alone. Considerable variation in sequence is evident, and when different Ω-conotoxin sequences were first compared, only the cysteine residues that are involved in disulfide bonding and one glycine residue were found to be invariant.

Another class of conotoxins found in C. geographus venom is that referred to as the conantokins which cause sleep in young mice and hyperactivity in older mice and are targeted to the NMDA receptor. Each cone venom appears to have its own distinctive group or signature of different conotoxin sequences.

Many of these peptides have now become fairly standard research tools in neuroscience. The μ-conotoxins, because of their ability to preferentially block muscle but not ax nal $Na^+$ channels, are convenient tools for immobilizing skeletal muscle without affecting ax nal or synaptic events. The Ω-conotoxins have become standard pharmacological reagents for investigating voltage-sensitive $Ca^{2+}$ channels and are used to block presynaptic termini and neurotransmitter release. The Ω-conotoxin GVIA from C. geographus venom, which binds to neuronal voltage-sensitive $Ca^{2+}$ channels, is an example of such. The affinity ($K_d$) of Ω-conotoxin GVIA for its high-affinity targets is subpicomolar; it takes more than 7 hours for 50% of the peptide to dissociate. Thus the peptide can be used to block synaptic transmission virtually irreversibly because it inhibits presynaptic $Ca^{2+}$ channels. However, Ω-conotoxin is highly tissue-specific. In contrast to the standard $Ca^{2+}$ channel-blocking drugs (e.g. the dihydropyridines, such as nifedipene and nitrendipene, which are widely used for angins and cardiac problems), which can bind $Ca^{2+}$ channels is smooth, skeletal, and cardiac muscle as well as neuronal tissue, Ω-conotoxins generally bind only to a subset of neuronal $Ca^{2+}$ channels, primarily of the N subtype. The discrimination ratio for Ω-conotoxin binding to voltage-sensitive $Ca^{2+}$ channels in neuronal versus nonneuronal tissue (e.g. skeletal or cardiac muscle) is greater than $10^8$ in many cases.

Additional conotoxin peptides having these general properties continue to be sought.

SUMMARY OF THE INVENTION

The present invention provides a group of bioactive conotoxin peptides which are extremely potent inhibitors of synaptic transmission at the neuromuscular junction and/or which are targeted to specific ion channels. They are useful as pesticides, and many of them or closely related analogs thereof are targeted to specific insects or other pests. Therefore, the DNA encoding such conotoxin peptides can be advantageously incorporated into plants as a plant-defense gene to reader plants resistant to specified pests.

The conotoxin peptides have the formulae set forth hereinafter. Moreover, examination of the formulae shows an indication of two new classes of conotoxin peptides in addition to those classes hereinbefore described. Class A includes peptides SEQ ID NO:1 to NO:6; each has 6 Cys residues which are interconnected by 3 disulfide linkages, with the 2 Cys residues nearest the N-terminus being part of a sequence -Cys-Cys-Gly-. All 6 members have at least one 4Hyp residue and a C-terminus which appears to be amidated. There are 2 amino acid (AA) residues separating the 3rd and 4th Cys as numbered (from the N-terminus) and a single AA residue spacing the 4th Cys from the 5th Cys. Moreover, the 2nd Cys is usually separated from the 3rd Cys by either 6 or 7 AA residues in this class, whereas there can be from about 3 to about 6 AA residues separating the 5th and 6th Cys residues. Class B is exemplified by SEQ ID NO:7, wherein there is a central sequence of 5 AA residues having 2 pairs of Cys residues flanking a center residue which is preferably Asn and wherein there are 2 additional pairs of spaced-apart Cys residues located, respectively. N-terminally and C-terminally of this central sequence. SEQ ID NO:8 appears to be a member of the known class of α-conotoxins. SEQ ID NO:9 appears to be a member of the known class of μ-conotoxins. SEQ ID NO:10 and NO:11 may be members of the class of Ω-conotoxins. SEQ ID NO:12 appears to be a member of the class of conantokins characterized by the N-terminal sequence Gly-Glu-Gla-Gla, and SEQ ID NO:13 may be a member of a heretofore uncharacterized class which causes sluggish behavior. The individual formulae of these conotoxins are as follows:

Gly-Cys-Cys-Gly-Ser-Tyr-Pro-Asn-Ala-Ala-Cys-His-Pro-Cys-Ser-Cys-Lys-Asp-Arg-Xaa-Ser-Tyr-Cys-Gly-Gln (SEQ ID NO:1) (J-020), wherein Xaa is 4Hyp (4-hydroxyproline) and the C-terminus is amidated;

Glu-Lys-Ser-Leu-Val-Pro-Ser-Val-Ile-Thr-Thr-Cys-Cys-Gly-Tyr-Asp-Xaa-Gly-Thr-Met-Cys-Xaa-Xaa-Cys-Arg-Cys-Thr-Asn-Ser-Cys (SEQ ID NO:2) (J-005) wherein Glu in the 1-position is pGlu, Xaa is 4Hyp and the C-terminus is amidated; Ser in the 7-position may be glycosylated;

Cys-Cys-Gly-Val-Xaa-Asn-Ala-Ala-Cys-Pro-Xaa-Cys-Val-Cys-Asn-Lys-Thr-Cys-Gly (SEQ ID NO:3) (OB-34) wherein Xaa is 4Hyp and the C-terminus is amidated;

Gly-Cys-Cys-Gly-Ser-Tyr-Xaa-Asn-Ala-Ala-Cys-His-Xaa-Cys-Ser-Cys-Lys-Asp-Arg-Xaa-Ser-Tyr-Cys-Gly-Gln (SEQ ID NO:4) (J-019) wherein Xaa is 4Hyp and the C-terminus is amidated;

Gly-Cys-Cys-Gly-Ser-Tyr-Xaa-Asn-Ala-Ala-Cys-His-Pro-Cys-Ser-Cys-Lys-Asp-Arg-Xaa-Ser-Tyr-Cys-Gly-Gln (SEQ ID NO:5) (J-026) wherein Xaa is 4Hyp and the C-terminus is amidated;

Cys-Cys-Gly-Val-Xaa-Asn-Ala-Ala-Cys-His-Xaa-Cys-Val-Cys-Lys-Asn-Thr-Cys (SEQ ID NO:6) (OB-26) wherein Xaa is 4Hyp and the C-terminus is amidated;

Gly-Xaa-Ser-Phe-Cys-Lys-Ala-Asp-Glu-Lys-Xaa-Cys-Glu-Tyr-His-Ala-Asp-Cys-Cys-Asn-Cys-Cys-Leu-Ser-Gly-Ile-Cys-Ala-Xaa-Ser-Thr-Asn-Trp-Ile-Leu-Pro-Gly-Cys-Ser-Thr-Ser-Ser-Phe-Phe-Lys-Ile (SEQ ID NO:7) (J-029) wherein Xaa is 4Hyp; the C-terminus may optionally be amidated;

Gly-Cys-Cys-Ser-His-Pro-Ala-Cys-Ser-Gly-Lys-Tyr-Gln-Xaa-Tyr-Cys-Arg-Xaa-Ser (SEQ ID NO:8) (OB-20) wherein Xaa is and the C-terminus is amidated;

His-Xaa-Xaa-Cys-Cys-Leu-Tyr-Gly-Lys-Cys-Arg-Arg-Tyr-Xaa-Gly-Cys-Ser-Ser-Ala-Ser-Cys-Cys-Gln (SEQ ID NO:9) (J-021) wherein Xaa is 4Hyp;

Cys-Lys-Thr-Tyr-Ser-Lys-Tyr-Cys-Xaa-Ala-Asp-Ser-Xaa-Cys-Cys-Thr-Xaa-Gln-Cys-Val-Arg-Ser-Tyr-Cys-Thr-Leu-Phe (SEQ ID NO:10) (J-010) wherein Xaa is Gla and the C-terminus is amidated;

Ser-Thr-Ser-Cys-Met-Glu-Ala-Gly-Ser-Tyr-Cys-Gly-Ser-Thr-Thr-Arg-Ile-Cys-Cys-Gly-Tyr-Cys-Ala-Tyr-Phe-Gly-Lys-Lys-Cys-Ile-Asp-Tyr-Pro-Ser-Asn (SEQ ID NO:11) (J-008);

Gly-Glu-Xaa-Xaa-Val-Ala-Lys-Met-Ala-Ala-Xaa-Leu-Ala-Arg-Xaa-Asn-Ile-Ala-Lys-Gly-Cys-Lys-Val-Asn-Cys-Tyr-Pro (SEQ ID NO:12) (J-017) wherein Xaa is Gla (γ-carboxyglutmate); and Glu-Ser-Glu-Glu-Gly-Gly-Ser-Asn-Ala-Thr-Lys-Lys-Pro-Tyr-Ile-Leu (SEQ ID NO:13) (J-004), wherein Glu in the 1-position is pGlu (pyroglutamic) and the C-terminus may be amidated; Thr may be glycosylated.

Accordingly in one aspect, the invention provides conotoxin peptides having the general formula: $Xaa_1$-Cys-Cys-Gly-$Xaa_2$-Cys-$Xaa_3$-$Xaa_4$-Cys-$Xaa_5$-Cys-$Xaa_6$-Cys-$Xaa_7$-$NH_2$ (SEQ ID NO:14) wherein $Xaa_1$ is des-$Xaa_1$ or Gly or pGlu-Lys-Ser-Leu-Val-Pro-Ser-Val-Ile-Thr-Thr; $Xaa_2$ is Ser-Tyr-Pro-Asn-Ala-Ala or Tyr-Asp-4Hyp-Gly-Thr-Met or Val-4Hyp-Asn-Ala-Ala or Ser-Tyr-4Hyp-Asn-Ala-Ala; $Xaa_3$ is His, 4Hyp or Pro; $Xaa_4$ is Pro or 4Hyp; $Xaa_5$ is Ser, Arg or Val; $Xaa_6$ is Lys-Asp-Arg-4Hyp-Ser-Tyr or Thr-Asn-Ser or Asn-Lys-Thr or Lys-Asn-Thr; and $Xaa_7$ is des-$Xaa_7$ or Gly or Gly-Gln.

In another aspect, the invention provides conotoxin peptides having 6 Cys residues interconnected by 3 disulfide bonds, with the 2 Cys residues nearest the N-terminus being part of the sequence Cys-Cys-Gly and with the 3rd, 4th and 5th residue being spaced apart by 2 residues and 1 residue, respectively, said two residues being selected from His, Pro and 4Hyp, said single residue being Ser, Arg or Val and with the C-terminus being amidated, said conotoxin binding to the acetylcholine receptor.

In yet another aspect, the invention provides conotoxin peptides having 8 Cys residues interconnected by 4 disulfide bonds with the central 4 Cys residues being part of the sequence Cys-Cys-Asn-Cys-Cys (SEQ ID NO:15), said conotoxin causing immediate paralysis where administered intercranially to laboratory mice.

These peptides, which are generally termed conotoxins, are sufficiently small to be chemically synthesized. General chemical syntheses for preparing the foregoing conotoxins are described hereinafter along with specific chemical syntheses of several conotoxins and indications of biological activities of these synthetic products. Various of these conotoxins can also be obtained by isolation and purification from specific conus species using the techniques described in U.S. Pat. No. 4,447,356 (May 8, 1984), the disclosure of which is incorporated herein by reference.

Many of these conotoxin peptides are extremely potent inhibitors of synaptic transmission at the neuromuscular junction, while at the same time lacking demonstrable inhibition of either nerve or muscle action potential propagation. They are considered useful to relax certain muscles during surgery.

The activity of each of these conotoxin peptides is freely reversible upon dilution or removal of the toxin from the affected muscle. Moreover, toxicity of the cyclic peptides is generally destroyed by agents which disrupt disulfide bonds in the cyclic conotoxins, suggesting that correct disulfide bonding appears essential for biological activity; however, correct folding and/or rearrangement of a conotoxin may occur in vivo so that in some cases the linear peptide may be administered for certain purposes. In general, however, the synthetic linear peptides fold spontaneously when exposed to air-oxidation at cold room temperatures to create the correct disulfide bonds to confer biological activity, and such processing is accordingly preferred. The conotoxins exhibit activity on a wide range of vertebrate animals, including humans, and on insects, and many are useful to reversibly immobilize a muscle or group of muscles in humans or other vertebrate species. Many of these conotoxins and derivatives thereof are further useful for detection and measurement of acetylcholine receptors and other specific receptors which are enumerated hereinafter with respect to various particular peptides.

Many of these conotoxin peptides are also useful in medical diagnosis. For example, an immunoprecipitation assay with radiolabeled Ω-conotoxin can be used to diagnose the Lambert-Eaton myasthenic syndrome, which is a disease in which autoimmune antibodies targeted to endogenous $Ca^{2+}$ channels are inappropriately elicited, thereby causing muscle weakness and autonomic dysfunction.

Various of these conotoxin peptides are further useful for the treatment of neuromuscular disorders and for rapid reversible immobilization of muscles in vertebrate species, including humans, thereby facilitating the setting of fractures and dislocations. These conotoxins generally inhibit synaptic transmission at the neuromuscular junction and bond strongly to the acetylcholine receptor of the muscle end plate, and many are therefore especially suitable for detection and assay of acetylcholine receptors. Such measurements are of particular significance in clinical diagnosis of myasthenia gravis, and various of these conotoxins, when synthesized with a radioactive label or as a fluorescent derivative, provide improved quantitation and sensitivity in acetylcholine receptor assays.

DETAILED DESCRIPTION OF THE PREFERRED EMBODIMENTS

Although the conotoxins can be obtained by purification from the enumerated cone snails, because the amounts of conotoxins obtainable from individual snails are very small, the desired substantially pure conotoxins are best practically obtained in commercially valuable amounts by chemical synthesis. For example, the yield from a single cone snail may be about 10 micrograms or less of conotoxin. By substantially pure is meant that the peptide is present in the substantial absence of other biological molecules of the same type; it is preferably present in an amount at least about 85% by weight and more preferably at least about 95% of such biological molecules of the same type which are present, i.e. waters, buffers and innocuous small molecules may be present. Chemical synthesis of biologically active conotoxin peptide depends of course upon correct determination of the amino acid sequence, and these sequences have now been determined and are set forth in the preceding summary.

Many of the conotoxins have approximately the same level of activity, and comparison of them suggests a reasonable tolerance for substitution near the carboxy terminus of these peptides. Accordingly, equivalent molecules can be created by the substitution of equivalent residues in this region, and such substitutions are useful to create particular invertebrate-specific conotoxins.

Cysteine residues are present in a majority of these conotoxins, and several of the conotoxins disclosed herein exhibit similar disulfide cross-linking patterns to that of erabutoxin, a known protein toxin of sea snake venom. The fact that biological activity of these particular compounds is destroyed by agents which break disulfide bonds, such as sodium borohydride or β-mercaptoethanol, indicates that a specific folded configuration induced by disulfide crosslinks, is essential for bioactivity of these particular conotoxins. It has been found that air-oxidation of the linear peptides for prolonged periods under cold room temperatures results in the creation of a substantial amount of the bioactive, disulfide-linked molecules. Therefore, the preferable procedure for making these peptides is to oxidize the linear peptide and then fractionate the resulting product, using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration, because the cross-linking and/or rearrangement which occurs in vivo has been found to create the biologically potent conotoxin molecule; however, because of the dilution resulting from the presence of other fractions of less biopotency, a somewhat higher dosage may be required.

These conotoxins disclosed herein generally inhibit synaptic transmission at the neuromuscular junction by binding the acetylcholine receptor at a muscle end plate. A particularly useful characteristic of a number of these conotoxins is their high affinity for particular macromolecular receptors, accompanied by a narrow receptor-target specificity. A major problem in medicine results from side effects which drugs very often exhibit, some of which are caused by the drug binding not only to the particular receptor subtype that renders therapeutic value, but also to closely related, therapeutically irrelevant receptor subtypes which can often cause undesirable physiological effects. In contrast to most drugs, these conotoxins generally discriminate among closely related receptor subtypes.

The peptides are synthesized by a suitable method, such as by exclusively solid-phase techniques, by partial solid-phase techniques, by fragment condensation or by classical solution couplings. The employment of recently developed recombinant DNA techniques may be used to prepare these peptides, particularly the longer ones containing only natural amino acid residues which do not require post-translational processing steps.

In conventional solution phase peptide synthesis, the peptide chain can be prepared by a series of coupling reactions in which the constituent amino acids are added to the growing peptide chain in the desired sequence. The use of various N-protecting groups, various coupling reagents, e.g., dicyclohexylcarbodiimide or carbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise "Methoden der Organischen Chemie (Houben-Weyl): Synthese von Peptiden", E. Wunsch (editor) (1974) Georg Thieme Verlag, Stuttgart, W. Ger. Techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. The fragment condensation method of synthesis is exemplified in U.S. Pat. No. 3,972,859 by U.S. Pat. No. 3,842,067 (Oct. 15, 1974) and U.S. Pat. No. 3,862,925 (Jan. 28, 1975).

Common to such chemical syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various of the residues having labile side chains.

As far as the selection of a side chain amino protecting group is concerned, generally one is chosen which is not removed during deprotection of the α-amino groups during the synthesis. However, for some amino acids, e.g. His, protection is not generally necessary. In selecting a particular side chain protecting group to be used in the synthesis of the peptides, the following general rules are followed: (a) the protecting group preferably retains its protecting properties and is not split off under coupling conditions (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology; however, when peptides are not so prepared, they are preferably prepared using the Merrifield solid phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. The preparation of the hydroxymethyl resin is described by Bodansky et al., Chem. Ind. (London) 38, 1597–98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis", supra. BHA and MBHA resin supports are commercially available and are generally used when the desired polypeptide being synthesized has an unsubstituted amide at the C-terminus. Thus, solid resin supports may be any of those known in the art, such as one having the formulae: —O—$CH_2$-resin support, —NH BHA resin support or —NH—MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 can be used, or should still other groups than the free acid be desired at the C-terminus, it may be preferable to synthesize the peptide using classical methods as set forth in the Houben-Weyl text.

The C-terminal amino acid, protected by Boc and by a side-chain protecting group, if appropriate, can be first coupled to a chloromethylated resin according to the procedure set forth in Chemistry Letters, K. Horiki et al. 165–168 (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke, "The Peptides", 1 pp 72–75, Academic Press (1965).

After removal of the α-amino protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCC).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke supra. in Chapter III and by Kapoor, J. Phar. Sci., 59, p 1–27 (1970).

Each protected amino acid or amino acid sequence is introduced into the solid phase reactor in about a twofold or more excess, and the coupling may be carried out in a medium of dimethylformamide (DMF): $CH_2Cl_2$ (1:1) or in DMF or $CH_2Cl_2$ alone. In cases where incomplete coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by E. Kaiser et al., Anal. Biochem. 34, 595 (1970). The coupling reactions can be performed automatically, as on a Beckman 990 automatic synthesizer, using a program such as that reported in Rivier et al. Biopolymers, 1978, 17, pp 1927–1938.

After the desired amino acid sequence has been completed, the intermediate peptide can be removed from the resin supported by treatment with a reagent, such as liquid hydrogen fluoride, which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride for cleaving, one or more scavengers, such as anisole, cresol, dimethyl sulfide, and methylethyl sulfide are included in the reaction vessel.

Cyclization of the linear peptide is preferably effected, as opposed to cyclizing the peptide while a part of the peptidoresin, to create bonds between Cys residues. To effect such a disulfide cyclizing linkage, the fully protected peptide can be cleaved from a hydroxymethylated resin or a chloromethylated resin support by ammonolysis, as is well known in the art, to yield the fully protected amide intermediate, which is thereafter suitably cyclized and deprotected; alternatively, deprotection as well as cleavage of the peptide from the above resins or a benzhydrylamine (BHA) resin or a methyl-benzhydrylamine (MBHA), can take place at 0° C. with hydrofluoric acid (HF), followed by air-oxidation under high dilution conditions.

Thus, in one aspect, the invention also provides a method for manufacturing a synthetic conotoxin peptide of interest by carrying out the following steps: (a) forming a peptide intermediate having the desired amino acid residue sequence and at least one protective group attached to a labile side chain of a residue such as Ser, Thr, Tyr, Asp, Glu, His, Cys, Arg or Lys and optionally having its C-terminus linked by an anchoring bond to resin support; (b) splitting off the protective group or groups and any anchoring bond from the peptide intermediate to form a linear peptide; (c) creating a cyclizing bond between Cys residues present in the linear peptide to create a cyclic peptide; and (d) if desired, converting the resulting cyclic peptide into a nontoxic salt thereof. Particular side chain protecting groups and resin supports are well known in the art and are disclosed in the earlier-referenced patents.

In order to illustrate specific preferred embodiments of the invention in greater detail, the following exemplary work is provided.

EXAMPLE 1

Conotoxin SEQ ID NO:1 (also referred to as J-020), having the chemical formula: H-Gly-Cys-Cys-Gly-Ser-Tyr-Pro-Asn-Ala-Ala-Cys-His-Pro-Cys-Ser-Cys-Lys-Asp-Arg-4Hyp-Ser-Tyr-Cys-Gly-Gln-$NH_2$ is synthesized by stepwise elongation from the carboxyl terminus, using the solid phase Merrifield peptide synthesis procedure. Operational details of this general procedure, which are not set forth hereinafter, can be found in Stewart, J. M. and Young, J., Solid Phase Peptide Synthesis, 2nd Ed., Pierce Chemical Co., Rockford, Ill., (1984), and in Rivier et al., U.S. Pat. No. 5,064,939 (Nov. 12, 1991) the disclosure of the latter of which is incorporated herein by reference.

A methylbenzhydrylamine resin is used as the solid phase support and facilitates production of the amidated peptide. Amino acid residues, in the form of their Boc (tert-butyloxycarbonyl) derivatives, are coupled successively to the resin using dicyclohexylcarbodiimide (DCC) as the coupling or condensing agent. At each cycle of stepwise amino acid addition, the Boc group is removed by acidolysis with 50 percent (v/v) trifluoroacetic acid (TFA) in methylene chloride, using an appropriate scavenger, such as 1,2 ethanedithiol, thereby exposing a new α-amino group for the subsequent coupling step. More specifically, when an automated machine and about 5 grams of resin are used, following the coupling of each amino acid residue, washing, deblocking and coupling of the next residue are preferably carried out according to the following schedule:

| STEP | REAGENTS AND OPERATIONS | MIX TIMES MIN. |
|---|---|---|
| 1 | $CH_2Cl_2$ wash-40 ml. (2 times) | 3 |
| 2 | Methanol (MeOH) wash-30 ml. (2 times) | 3 |
| 3 | $CH_2Cl_2$ wash-80 ml. (3 times) | 3 |
| 4 | 50 percent TFA plus 5 percent 1,2-ethanedithiol in $CH_2Cl_2$-70 ml. (2 times) | 12 |
| 5 | Isopropanol wash-40 ml. (2 times) | 3 |
| 6 | TFA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc-amino acid (10 mmoles) in 30 ml. of either DMF or $CH_2Cl_2$, depending upon the solubility of the particular protected amino acid, (1 time) plus DCC (10 mmoles) in $CH_2Cl_2$ | 30–300 |

Side chain protecting groups are generally chosen from among the standard set of moderately acid-stable derivatives. Such protecting groups are preferably ones that are not removed during deblocking by trifluoroacetic acid in methylene chloride; however, all are cleaved efficiently by anhydrous hydrofluoric acid (HF) to release the functional side chains. Cysteine residues in positions 2, 3, 11, 14, 16 and 23 of the peptide are protected by p-methoxy-benzyl (Mob) groups so as to expose sulfhydryls upon deprotection. The phenolic hydroxyl group of Tyr is protected by 2-bromobenzyloxycarbonyl (Brz). The side chain of 4-hydroxyproline (4Hyp) is protected by benzyl ether (OBzl), and it is commercially available in this protected form. The side chain of Arg is protected with Tos (p-toluenesulfonyl). The side chain of Asp is protected as the cyclohexyl ester (OChx), and the primary amino side chain of Lys is protected with 2-chlorobenzyloxycarbonyl (Clz). The imidazole nitrogen of His is protected by Tos. Serine is protected by benzyl ether (OBzl). Asn is coupled without side chain protection in the presence of hydroxybenzotriazole (HOBt).

At the end of the synthesis, the following peptide intermediate is obtained: Boc-Gly-Cys(Mob)-Cys(Mob)-Gly-Ser(OBzl)-Tyr(Brz)-Pro-Asn-Ala-Ala-Cys(Mob)-His(Tos)-Pro-Cys(Mob)-Ser(OBzl)-Cys(Mob)-Lys(Clz)-Asp(OChx)-Arg(TOS-4Hyp(Bzl)-Ser(OBzl)-Tyr(Brz)-Cys(Mob)-Gly-Gla-MBHA resin support. All the side-chain blocking groups are HF-cleavable.

After removing the N-terminal Boc group with TFA, the linear peptide is cleaved from the resin and deprotected with HF, using 150 milliliters of HF, 16 ml of anisole and about 4 ml dimethyl sulfide for about 1.5 hours at 0° C., which removes all the remaining protecting groups. Any volatiles are removed by the application of a vacuum, and the peptide is washed with ethylether and then dissolved in 5 percent acetic acid. The solution is then diluted to about 15 liters and pH is adjusted to about 8.0 with diisopropyl ethylamine. It is exposed to air-oxidation is a cold room at about 4° C. for 4 days to form the disulfide cross links or bridges. One drop of mixture is recovered about every 12 hours and added to one drop of a solution containing dithio-bis(2-nitrobenzoic) acid in a molar buffer of $K_2HPO_4$ (pH 8) in order to follow the progress of the oxidation reaction (Ellman test). During the whole reaction, the pH was maintained at 8 by addition of diisopropylethylamine. After 50 hours, the absence of yellow coloration is observed in the test with dithio-bis(2-nitrobenzoic acid).

After formation of the disulfide bridges, the cyclized pool of peptides is applied to a Bio-Rex-70 column (5×15 cm), washed in distilled water (100 ml), and eluted with 50% acetic acid. The cyclized peptide fractions are collected and lyophilized.

The lyophilized peptide fractions are then purified by preparative or semi-preparative HPLC as described in Rivier, et al., J. Chromatography, 288, 303–328 (1984); and Hoeger, et al., BioChromatography, 2, 3, 134–142 (1987). The chromatographic fractions are carefully monitored by HPLC, and only the fractions showing substantial purity are pooled.

The peptide is judged to be homogeneous by reversed-phase high performance liquid chromatography using a Waters HPLC system with a 0.46×25 cm. column packed with 5 μm $C_{18}$ silica, 300 Å pore size. The determination is run at room temperature using gradient conditions with 2 buffers. Buffer A is an aqueous trifluoroacetic acid (TFA) solution consisting of 1.0 ml of TFA per 1000 ml. of solution. Buffer B is 1 ml TFA diluted to 400 ml with $H_2O$ which is added to 600 ml. of acetonitrile. The analytical HPLC was run under gradient conditions which vary uniformly from 20 volume percent (v/o) Buffer B to 35 v/o Buffer B over 10 minutes, at a constant flow rate of 2 ml. per minute; the retention time for the biologically active cyclic conotoxin is 10.6 minutes.

The product is also characterized by amino acid analysis and by toxicity tests. One microgram of the synthetic toxin injected intracerebrally (IC) in a mouse is lethal in less than 10 minutes showing that the synthetic product is highly toxic, and thus synthesis by the described method, if followed by air-oxidation, achieves the correct disulfide pairing arrangement to assure biological activity. The synthetic peptide is shown to be substantially identical with the native conotoxin as a result of coelution on HPLC, amino acid analysis and biological activity. This peptide binds to and inhibits the function of the acetylcholine receptor, thereby causing paralysis and thereafter death. It can be used in assays for the acetylcholine receptor.

EXAMPLE 2

Conotoxin SEQ ID NO:2 (also referred to as J-005), having the chemical formula: H-pGlu-Lys-Ser-Leu-Val-Pro-Ser-Val-Ile-Thr-Thr-Cys-Cys-Gly-Tyr-Asp-4Hyp-Gly-Thr-Met-Cys-4Hyp-4Hyp-Cys-Arg-Cys-Thr-Asn-Ser-Cys-$NH_2$ is synthesized by stepwise elongation from the carboxyl terminus, using the solid phase synthesis procedure as set forth in Example 1 and the same methyl benzyhydrylamine resin.

The side chains of hydroxyproline, threonine and serine are protected by benzyl ether (Bzl).

At the end of the synthesis, the following peptide intermediate is obtained: Boc-pGlu-Lys(Clz)-Ser(Bzl)-Leu-Val-Pro-Ser(Bzl)-Val-Ile-Thr(Bzl)-Thr(Bzl)-Cys(Mob)-Cys(Mob)-Gly-Tyr(Brz)-Asp(OChx)-4Hyp(Bzl)-Gly-Thr(Bzl)-Met-Cys(Mob)-4Hyp(Bzl)-4Hyp(Bzl)-Cys(Mob)-Arg(Tos)-Cys(Mob)-Thr(Bzl)-Asn-Ser(Bzl)-Cys(Mob)-MBHA resin support. All the side-chain blocking groups are HF-cleavable.

After removing the N-terminal Boc group with TFA, the linear peptide is cleaved from 3 grams of the resin and deprotected, using 100 milliliters of HF, 1 ml of anisole and about 4 ml dimethyl sulfide for about 1.5 hours at 0° C., which removes all the remaining protecting groups. Any volatiles are removed by the application of a vacuum, and the peptide is washed with ethylether and then extracted with 10 percent acetic acid containing 10% cyanomethane. The solution is then diluted to about 4 liters and a pH of about 6.95. The solution is exposed to air-oxidation in a cold room at about 4° C. for a time sufficient to completely oxidize by forming disulfide crosslinks or bridges, i.e., a period of about 1 to 2 weeks.

After formation of the disulfide bridges, the cyclized pool of peptides is applied to a Bio-Rex-70 column (5×15 cm) an eluted with 50% acetic acid. The cyclized peptide fractions are collected and lyophilized. The synthetic peptide is shown to be substantially identical with the native conotoxin as a result of coelution on HPLC, amino acid analysis and biological activity, which comparison is made with the native conotoxin following deglycosylation to remove the carbohydrate linked to Ser in the 7-position which increases bioactivity.

When injected IC into mice, the peptide causes mice to become spastic and to suffer paralysis. It is thus known to have high affinity and specificity for a particular receptor and can be used to target this receptor and in assays for this receptor.

EXAMPLE 3

The peptide OB-34 (SEQ ID NO:3) is produced by using the synthesis as generally set forth in Example 1. The peptide in question has the following formula: H-Cys-Cys-Gly-Val-4Hyp-Asn-Ala-Ala-Cys-Pro-4Hyp-Cys-Val-Cys-Asn-Lys-Thr-Cys-Gly-$NH_2$ The synthesis is carried out on an MBHA resin, and Boc is used to protect the α-amino groups. The same side chain protecting units are used as described hereinbefore.

About 4½ grams of the peptide-resin is treated with 5 milliliters of anisole, 1 milliliter of methylethyl sulfide, and 60 milliliters of HF for ½ hour at −20° C. and 1 hour at 0° C. The peptide is then extracted and dissolved in 4.5 liters of ammonium acetate buffer, a solution containing about 10 grams of ammonium acetate at a pH of about 4.3 pH is adjusted to about 7.75 with ammonium hydroxide, and the solution is maintained in a cold room at about 4° C. for a sufficient length of time to allow complete air-oxidation to occur. Purification is then carried out as previously described with respect to Example 2, and the purified peptide is subjected to analytical HPLC. It is found to exhibit a single peak with both a gradient flow and with isocratic flow of appropriate buffers. The purity of the compound was estimated to be greater than about 99 percent. The synthetic peptide coelutes with the native peptide on HPLC.

Injection of 1 microgram of the synthetic peptide OB-34 intracerebrally into a mouse shows that the mouse exhibits a reproducible physical effect indicative of binding to a specific receptor and confirms that the air-oxidation produces appropriate cross-linking so that the synthetic conotoxin exhibits biological potency. It is thus known to have high affinity and specificity for a particular receptor and can be used to target this receptor and in assays for this receptor.

EXAMPLE 4

The peptide J--019 (SEQ ID NO:4) is synthesized using the procedure as described with respect to Example 1. The synthetic peptide has the following formula: H-Gly-Cys-Cys-Gly-Ser-Tyr-4Hyp-Asn-Ala-Ala-Cys-His-4Hyp-Cys-Ser-Cys-Lys-Asp-Arg-4Hyp-Ser-Tyr-Cys-Gly-Gln-$NH_2$ An MBHA resin is used, and Boc is used to protect the α-amino groups of each of the amino acids employed in the synthesis. Side chain protecting groups as set forth with respect to Example 1 are similarly employed. Cleavage from the resin and air-oxidation to carry out cyclicization are performed as set forth in Example 1.

The cyclic peptide is purified using the procedure set forth in Example 1 and checked for purity via analytical HPLC, which shows that a substantially pure synthetic material is obtained. The synthetic peptide is shown to be substantially identical with the native conotoxin as a result of coelution on HPLC, amino acid analysis and biological activity. Injection of the peptide intracerebrally into a mouse shows an initial attack of violent scratching followed by paralysis and ultimate death, confirming that air-oxidation can produce appropriate cross-linking so that the synthetic conotoxin exhibits biological potency. It is thus known to have high affinity and specificity for a particular receptor and can be used to target this receptor and in assays for this receptor.

EXAMPLE 5

The procedure of Example 4 is repeated with a single change of the amino acid in the 13-position to substitute proline for 4-hydroxyproline and thereby synthesize the peptide J-026 (SEQ ID NO:5). The synthetic peptide has the following formula: H-Gly-Cys-Cys-Gly-Ser-Tyr-4Hyp-Asn-Ala-Ala-Cys-His-Pro-Cys-Ser-Cys-Lys-Asp-Arg-4Hyp-Ser-Tyr-Cys-Gly-Gln-$NH_2$ Cleavage from the resin and air-oxidation to carry out cyclicization are performed as set forth in Example 1.

Analytical HPLC shows the substantially pure compound is obtained. The synthetic peptide is shown to be substantially identical with the native conotoxin as a result of coelution on HPLC, amino acid analysis and biological activity. Testing by IC injection into a mouse gives a similar biological result to that obtained in Example 10, i.e., violent scratching followed by paralysis and death. It is thus known to have high affinity and specificity for a particular receptor and can be used to target this receptor and in assays for this receptor.

EXAMPLE 6

The synthesis of peptide OB-26 (SEQ ID NO:6) is carried out using a procedure generally the same as that described with respect to Examples 1 and 3. The synthetic peptide has the following formula: H-Cys-Cys-Gly-Val-4Hyp-Asn-Ala-Ala-Cys-His-4Hyp-Cys-Val-Cys-Lys-Asn-Thr-Cys-$NH_2$ Cleavage from the MBHA resin and air-oxidation are carried out as set forth in Example 1. HPLC purification of the cross-linked peptide is carried out in a similar manner. The resultant synthetic peptide is checked by analytical HPLC and shown to constitute a substantially pure compound. The synthetic peptide is shown to be substantially identical with the native conotoxin as a result of coelution on HPLC, amino acid analysis and biological activity. Injection of 1 microgram of the synthetic peptide IC into a mouse results in a reproducible physical effect, which verifies that the appropriate disulfide linkages are achieved during the air-oxidation step. It is believed that the peptide has high affinity and specificity for a particular receptor and that it can be used to target this receptor and to assay for this receptor.

EXAMPLE 7

Synthesis of the peptide J-029 (SEQ ID NO:7) is carried out on a chloromethylated resin in the same general manner as set forth in Example 6. The synthetic peptide has the following formula: H-Gly-4Hyp-Ser-Phe-Cys-Lys-Ala-Asp-Glu-Lys-4Hyp-Cys-Glu-Tyr-His-Ala-Asp-Cys-Cys-Asn-Cys-Cys-Leu-Ser-Gly-Ile-Cys-Ala-Hyp-Ser-Thr-Asn-Trp-Ile-Leu-Pro-Gly-Cys-Ser-Thr-Ser-Ser-Phe-Phe-Lys-Ile-OH The peptide is cleaved from the resin with anisole, methylethyl sulfide and HF, and air-oxidation is then carried out under the condition as generally set forth in Example 1 in order to obtain the cyclic compound. Thereafter, purification is carried out using HPLC as set forth hereinbefore. Ultimate subjection of the purified peptide to analytical HPLC shows that a substantially pure compound is obtained. The synthetic peptide is shown to be substantially identical with the native conotoxin as a result of coelution on HPLC, amino acid analysis and biological activity.

Injection of a dose of about 1 microgram of the synthetic conotoxin IC into a mouse shows substantially immediate paralysis occurring. It is thus known to have high affinity and specificity for a particular receptor and can be used to target this receptor and in assays for this receptor.

EXAMPLE 8

The synthesis of peptide OB-20 (SEQ ID NO:8) having the formula: H-Gly-Cys-Cys-Ser-His-Pro-Ala-Cys-Ser-Gly-Lys-Tyr-Gln-Gla-Tyr-Cys-Arg-Gla-Ser-$NH_2$ is carried out generally as set forth in Example 3 using an Fmoc strategy on a 2,4-dimethoxy-alkoxybenzyl amine resin.

The peptide is cleaved from the resin using a mixture of TFA, thioanisole, water and DCM in the following volume ratios: 40:10:1:44. Cleavage is carried out for about 8 hours at 37° C. Following cleavage, air-oxidation is carried out to cyclize the peptide as set forth in Example 1.

Purification of the cyclized peptide is carried out as set forth hereinbefore. Subjection of the purified peptide to HPLC and amino acid analysis shows that a peptide having a purity of greater than 95 percent is obtained, which has the expected ratio of residues when subjected to amino acid analysis. The synthetic peptide coelutes with the native peptide on HPLC.

Injection of 1 microgram of the synthetic peptide OB-20 intracerebrally into a mouse shows that the mouse exhibits a reproducible physical effect and confirms that air-oxidation produces appropriate cross-linking so that the synthetic conotoxin exhibits biological potency. It is thus known to have high affinity and specificity for a particular receptor and can be used to target this receptor and in assays for this receptor.

EXAMPLE 9

A synthesis, as generally set forth in Example 1, is carried out using about 25 grams of a chloromethylated polystyrene resin of the type generally commercially available to produce peptide J-021 (SEQ ID NO:9) which has the following formula: H-His-4Hyp-4Hyp-Cys-Cys-Leu-Tyr-Gly-Lys-Cys-Arg-Arg-Tyr-4Hyp-Gly-Cys-Ser-Ser-Ala-Ser-Cys-Cys-Gln-OH.

Similar side chain protecting groups are provided as described in Example 1, and the hydroxyl side chain of 4-hydroxyproline is protected as the benzyl ether. Coupling of the N-terminal His residue is carried out using Boc-His (Tos) dissolved in DMF and using about 3 millimoles of benzotriazol-1-yl-oxy-tris(dimethylamino)phosphonium hexafluorophosphate (BOP) as a coupling agent.

After the final His residue is coupled to the peptide-resin, the Boc group is removed using 45 percent TFA in methylene chloride. The peptide-resin is then treated with anisole and methylethyl sulfide and HF. Five grams of resin are treated with 10 milliliters of anisole, one ml of methylethyl sulfide and 125 ml of HF for ½ hour at −20° C. and 1 hour at 0° C. The cleaved peptide is then extracted using 200 milliliters of 50 percent acetic acid at a temperature below 0° C. Thereafter, the extracted peptide is dissolved in 8 liters of 1 percent ammonium acetate at a pH of about 4.35. The pH is raised to about 7.74 with ammonium hydroxide, and air-oxidation is effected as described in Example 1.

Purification is carried out as described in Example 1, and then purity is checked using analytical HPLC. The peptide is applied to a reversed phase $C_{18}$ column, and then eluted by subjecting the column to a gradient of buffers A and B at a flow rate of about 0.21 milliliters per minute, which gradient changes uniformly from 0 percent buffer B to 20 percent buffer B over a time period of 20 minutes. Buffer A is a 1 percent aqueous solution of TFA, and buffer B is 0.1% TFA and 70% acetonitrile. This HPLC shows that the peptide elutes at about 18.6 minutes and has a purity of greater than 99 percent. The synthetic peptide coelutes with the native peptide on HPLC. Amino acid analysis of the pure peptide shows that the expected residues are obtained.

It is believed that testing will show this peptide to have high affinity and specificity for a particular receptor so that it can be used to target this receptor or to assay for this receptor.

EXAMPLE 10

The peptide J-010 (SEQ ID NO:10) is synthesized using the procedure as generally set forth with respect to Example 8 using an Fmoc protection strategy. The synthetic peptide has the following formula: H-Cys-Lys-Thr-Tyr-Ser-Lys-Tyr-Cys-Gla-Ala-Asp-Ser-Gla-Cys-Cys-Thr-Gla-Gln-Cys-Val-Arg-Ser-Tyr-Cys-Thr-Leu-Phe-$NH_2$.

The peptide is cleaved from the resin using a mixture of TFA, thioanisole, water and DCM in the following volume ratios: 40:10:1:44. Cleavage is carried out for about 8 hours at 37° C. Following cleavage, air-oxidation is carried out to cyclize the peptide as previously described.

Purification of the cyclized peptide is carried out as set forth hereinbefore, and subjection of the purified peptide to HPLC shows that a substantially pure peptide is obtained. The synthetic peptide is shown to be substantially identical with the native conotoxin as a result of coelution on HPLC, amino acid analysis and biological activity. Injection of about 1 microgram of the synthetic peptide intracerebrally into a mouse shows that the mouse begins rapid running and stretching, ultimately resulting in death. It is thus known to have high affinity and specificity for a particular receptor and can be used to target this receptor and in assays for this receptor.

EXAMPLE 11

A synthesis as generally performed in Example 1 is carried out to produce peptide J-008 (SEQ ID NO:11) having the formula: H-Ser-Thr-Ser-Cys-Met-Glu-Ala-Gly-Ser-Thr-Cys-Gly-Ser-Thr-Thr-Arg-Ile-Cys-Cys-Gly-Tyr-Cys-Ala-Tyr-Phe-Gly-Lys-Lys-Cys-Ile-Asp-Tyr-Pro-Ser-Asn-OH.

The C-terminal residue in the peptide is Asn in its free acid form. An MBHA resin was used along with the incorporation of Boc-protected Asp through its β-carboxylic group.

Cleavage from the resin and cyclization is carried out as in Example 1. The final product is similarly purified to homogeneity by HPLC, and amino acid analysis of the purified peptide gives the expected results. The synthetic peptide coelutes with the native peptide on HPLC.

The synthetic toxin is injected IC into a mouse, and it proves lethal in less than 10 minutes, confirming that the synthetic product is highly toxic and that the stated synthesis produces a compound having biological activity. It is thus known to have high affinity and specificity for a particular receptor and can be used to target this receptor and in assays for this receptor.

EXAMPLE 12

Synthesis of conotoxin SEQ ID NO:12 (also referred to as J-017), having the formula: H-Gly-Glu-Gla-Gla-Val-Ala-Lys-Met-Ala-Ala-Gla-Leu-Ala-Arg-Gla-Asn-Ile-Ala-Lys-Gly-Cys-Lys-Val-Asn-Cys-Tyr-Pro-OH is carried out generally similarly to that of Example 1 but using the modifications described hereinafter.

A commercially available p-alkoxybenzyl alcohol resin is used for the synthesis, which is a standard resin used in solid phase syntheses employing the Fmoc-amino acid strategy. Fluorenylmethyloxycarbonyl (Fmoc) is used to protect the α-amino groups of each of the amino acids, and Boc protection is used for the side-chain amino groups of Lys. The Tyr side chain is protected by O-tBu, and the Cys side chain is protected by diphenylmethyl (trityl). The carboxyl side chain of Glu and the side chains of Gla are protected by O-t-Bu as described hereinafter. Arg is protected by 4-methoxy-2,3,6-trimethylbenzenesulfonyl (Mtr).

Fmoc-L-Gla(O-t-Bu)$_2$-OH is prepared as set forth hereinafter. Condensation of Z-L-Ser(Tos)-$OCH_3$ with di-tert-butyl malonate, to give Z-DL-Gla(O-t-Bu)$_2$-$OCH_3$ is carried out by a modification of the procedure of Rivier et al. Biochemistry 26, 8508–8512 (1987). Sodium hydride is rinsed twice with pentane, suspended in absolute benzene, and then added to the benzene solution of di-tert-butyl malonate. The reaction is allowed to proceed to completion with 10 minutes of reflux. The resulting suspension is cooled in an ice bath, and the Z-L-Ser(Tos)-$OCH_3$ dissolved in benzene/tetrahydrofuran is added under an argon atmosphere with vigorous stirring and continued cooling at 0° C. for 2 hours. Stirring is maintained for additional 48 hours at room temperature. At this time, the suspension is cooled and washed successively with ice water. 1N HCl, and water. After rotary evaporation at room temperature, the oil is dissolved in benzene, and pentane is added to initiate crystallization. The yield is 40–60% for a preparation of 0.5 mole. The methyl ester is hydrolyzed by dissolving in alcohol and adding 1,2 equiv of KOH dissolved in water/ethanol. The solution is allowed to remain at room temperature for several days; the reaction is monitored by HPLC using a $C_{18}$ 5-μm column, with 0.1% TFA-acetonitrile as the solvent. When the reaction is complete, the solution is evaporated at room temperature, and the product extracted with ethyl acetate after the addition of $NaHSO_4$. The ethyl acetate extract is dried over $Na_2SO_4$ and evaporated under reduced pressure; the yield is 80–90%.

The D- and L-isomers are resolved by crystallization of the quinine salt of the D-isomer. Z-DL-di-t-Bu-Gla-OH in ethyl acetate is reacted with an equivalent amount of quinine. The crystals are separated from the mother liquid, and the Z-D-di-t-Bu-Gla-OH is recrystallized from ethyl acetate. The quinine salt is suspended in ether, and quinine is removed by the addition of a 20% citric acid solution at 0° C. The same process is used to remove quinine from the liquid phase. The L-isomer is precipitated in the form of its ephedrine salt from ethyl acetate-pentane and recrystallized (Marki et al., Helv. Chim. Acta. 60, 798–800, 1977). Elimination of ephedrine by acid extraction, hydrogenation of the Z group, and introduction of the Fmoc are all standard laboratory procedures. Optical purity of the L- and D-isomers of Fmoc-Gla(O-t-Bu)$_2$-OH is assessed after hydrolysis to Glu (6N HCl, 110° C., 20 hours), and each is approximately 99% pure.

The coupling of the Fmoc-protected amino acids to the resin is accomplished using a schedule generally similar to that set forth in Example 1 but removing the Fmoc group via the use of a 20 percent solution (v/v) of freshly distilled piperidine in dimethylformamide (DMF) for 10 minutes. Thorough resin washing is accomplished by repeated application of DMF, methanol, or dichloromethane (DCM). Couplings are mediated by DCC in either DCM, DMF, or mixtures thereof, depending upon the solubility of the particular amino acid derivative. Fmoc-Asn is incorporated into the peptide with an unprotected side chain, in the presence of 2 equiv of HOBT, and is coupled in DMSO/DMF or DMSO/DCM.

The peptide is released from 4 grams of the peptide resin as the C-terminal free acid by treatment with a freshly prepared mixture of TFA, thioanisole, $H_2O$, EDT and DCM (40/18/1/2/49) (40 ml) at about 37° C. for 6–8 hours. Trial cleavages on small amounts demonstrate that the peptide is freed and that all side-chain protection, including the difficult Mtr group, are removed while Gla remains intact.

The peptide is precipitated from the cleavage solution after extraction with methyl tert-butyl ether. The peptide is then dissolved in distilled water, the pH of the resulting solution is adjusted to approximately 7–8 with dilute ammonium hydroxide, after separating the resin by filtration. Formation of the disulfide cross-link is carried out on the crude peptide product using a liquid phase, air-oxidation step in a cold room as described with respect to Example 1. The crude peptide is purified by preparative HPLC using a preparative cartridge (15–20 μm, 300 Å Vydac $C_{18}$) and a TEAP buffer, pH 2.25, and also with a 0.1% TFA buffer using appropriate gradients of acetonitrile. Highly purified fractions are pooled and lyophilized, yielding peptide as its TFA salt. Optical rotation in 1% acetic acid measures $[\alpha]_D$=−64° (c=1) at 20° C. Amino acid analysis gives the expected values. FAB mass spectrometry is performed on the peptide, and the spectrum shows a protonated molecular ion ($MH^+$) at m/z=3097.4 corresponding to the calculated monoisotopic peptide of 3097.36. A chromatogram of the crude preparation after TFA cleavage and deprotection illustrates that the major product is particularly pure and that only a relatively small amount of hydrophobic impurities are present. Sequence analysis gives the expected residue at each cycle, except for blanks with Gla residues, confirming that the pure target peptide is obtained. The synthetic peptide coelutes with the native peptide on HPLC.

When injected IC into young mice, it causes sleeping; however, when injected into older mice, it causes hyperactivity. It is thus known to have high affinity and specificity for a particular receptor and can be used to target this receptor and in assays for this receptor, tentatively identified as the NMDA receptor.

EXAMPLE 13

A synthesis of the linear peptide J-004 (SEQ ID NO:13) is carried out on an MBHA resin using the procedure as generally set forth in Example 1. The linear peptide J-004 has the following formula: H-Glu-Ser-Glu-Glu-Gly-Gly-Ser-Asn-Ala-Thr-Lys-Lys-Pro-Tyr-Ile-Leu-$NH_2$.

The ultimate linear peptide is purified and subjected to amino acid analysis; it shows that the expected residues are obtained in the peptide sequence. The synthetic peptide coelutes with the native peptide on HPLC, after the native conotoxin has been deglycosylated to remove the carbohydrate which is linked to Thr in the 10-position which appears to increase bioactivity. Testing of the synthetic peptide by injection IC into a mouse shows that the mouse quickly becomes sluggish and unable to stand or function normally, which demonstrates that the synthetic peptide has the expected biological potency. It is thus known to have high affinity and specificity for a particular receptor and can be used to target this receptor and in assays for this receptor.

These synthetic peptides, for administration to humans, should have a purity of at least about 95 percent (herein referred to a substantially pure), and preferably have a purity of at least about 98 percent. Purity for purposes of this application refers to the weight of the intended peptide as compared to the weight of all peptide fragments present. These synthetic peptides, either in the free form or in the form of a nontoxic salt, are commonly combined with a pharmaceutically or veterinarily acceptable carrier to create a composition for administration to animals, including humans, or for use in in vitro assays. In vivo administration should be carried out by a physician and the required dosage will vary with the particular objective being pursued. In this respect, guidelines have been developed for the use of other conotoxins such as conotoxin GI and such are well known in this art are employed for the particular purpose of use.

As indicated hereinbefore, DNA encoding the amino acid structure of any of these conotoxins can be used to produce the proteins recombinantly as well as to afford different varieties of plants with pesticidal properties.

To synthesize a protein having the desired conotoxin amino acid residue sequence by recombinant DNA, a double-stranded DNA chain which encodes the sequence might be synthetically constructed. Although it is nowadays felt that PCR techniques would be the method of choice to produce DNA chains, a DNA chain encoding the desired sequence could be designed using certain particular codons that are more efficient for polypeptide expression in a certain type of organism, i.e. selection might employ those codons which are most efficient for expression in the type of organism which is to serve as the host for the recombinant vector. However, any correct set of codons will encode a desired product, although perhaps slightly less efficiently. Codon selection may also depend upon vector construction considerations; for example, it may be necessary to avoid placing a particular restriction site in the DNA chain if, subsequent to inserting the synthetic DNA chain, the vector is to be manipulated using the restriction enzyme that cleaves at such a site. Also, one should of course avoid placing restriction sites in the DNA chain if the host organism, which is to be transformed with the recombinant vector containing the DNA chain, is known to produce a restriction enzyme that would cleave at such a site within the DNA chain.

To assemble such a synthetic, nonchromosomal, conotoxin-encoding DNA chain, oligonucleotides are constructed by conventional procedures such as those described in J. Sambrook et al., Molecular Cloning, A Laboratory Manual, Cold Spring Harbor Laboratory Press, New York (1989) (hereinafter, Sambrook et al.). Sense and antisense oligonucleotide chains, up to about 70 nucleotide residues long, are synthesized, preferably on automated synthesizers, such as the Applied Biosystem Inc. Model 380A DNA synthesizer. The oligonucleotide chains are constructed so that portions of the sense and antisense oligonucleotides overlap, associating with each other through hydrogen bonding between complementary base pairs and thereby forming double stranded chains, in most cases with gaps in the strands. Subsequently, the gaps in the strands are filled in, and oligonucleotides of each strand are joined end to end with nucleotide triphosphates in the presence of appropriate DNA polymerases and/or with ligases.

As an alternative to such stepwise construction of a synthetic DNA chain, the cDNA corresponding to the desired conotoxin may be cloned. As is well known, a cDNA library or an expression library is produced in a conventional manner by reverse transcription from messenger RNA (mRNA) from suitable tissue from the cone snail of interest. To select clones containing desired sequences, a hybridization probe or a mixed set of probes which accommodate the degeneracy of the genetic code and correspond to a selected portion of the protein of interest are produced and used to identify clones containing such sequences. Screening of such an expression library with antibodies made against the protein may also be used, either alone or in conjunction with hybridization probing, to identify or confirm the presence of DNA sequences in cDNA library clones which are expressing the protein of interest. Such techniques are taught, for example in Sambrook et al., supra.

In addition to the protein-encoding sequences, a DNA chain should contain additional sequences depending upon vector construction considerations. Typically, a synthesized DNA chain has linkers at its ends to facilitate insertion into restriction sites within a cloning vector. A DNA chain may be constructed so as to encode the protein amino acid sequences as a portion of a fusion polypeptide; and if so, it will generally contain terminal sequences that encode amino acid residue sequences that serve as proteolytic processing sites, whereby the desired polypeptide may be proteolytically cleaved from the remainder of the fusion polypeptide. The terminal portions of the synthetic DNA chain may also contain appropriate start and stop signals.

Accordingly, a double-stranded conotoxin-encoding DNA chain is constructed or modified with appropriate linkers for its insertion into a particular appropriate cloning vectors. The cloning vector that is to be recombined to incorporate the DNA chain is selected appropriate to its viability and expression in a host organism or cell line, and the manner of insertion of the DNA chain depends upon factors particular to the host. For example, if the DNA chain is to be inserted into a vector for insertion into a prokaryotic cell, such as E. coli, the DNA chain will be inserted 3' of a promoter sequence, a Shine-Delgarno sequence (or ribosome binding site) that is within a 5' non-translated portion and an ATG start codon. The ATG start codon is appropriately spaced from the Shine-Delgarno sequence, and the encoding sequence is placed in correct reading frame with the ATG start codon. The cloning vector also provides a 3' non-translated region and a translation termination site. For insertion into a eukaryotic cell, such as a yeast cell or a cell line obtained from a higher animal, the conotoxin-encoding oligonucleotide sequence is appropriately spaced from a capping site and in correct reading frame with an ATG start signal. The cloning vector also provides a 3' non-translated region and a translation termination site.

Prokaryotic transformation vectors, such as pBR322, pMB9, Col E1, pCR1, RP4 and lambda-phage, are available for inserting a DNA chain of the length which encodes conotoxin with substantial assurance of at least some expression of the encoded polypeptide. Typically, such vectors are constructed or modified to have one or more unique restriction sites appropriately positioned relative to a promoter, such as the lac promoter. The DNA chain may be inserted with appropriate linkers into such a restriction site, with substantial assurance of production of desired protein in a prokaryotic cell line transformed with the recombinant vector. To assure proper reading frame, linkers of various lengths may be provided at the ends of the protein-encoding sequences. Alternatively, cassettes, which include sequences, such as the 5' region of the lac Z gene (including the operator, promoter, transcription start site. Shine-Delgarno sequence and translation initiation signal), the regulatory region from the tryptophane gene (trp operator, promoter, ribosome binding site and translation initiator), and a fusion gene containing these two promoters called the trp-lac or commonly called the Tac promoter are available into which the synthetic DNA chain may be conveniently inserted and then the cassette inserted into a cloning vector of choice.

Similarly, eukaryotic transformation vectors, such as, the cloned bovine papilloma virus genome, the cloned genomes of the murine retroviruses, and eukaryotic cassettes, such as the pSV-2 gpt system (described by Mulligan and Berg, Nature 277, 108–114, 1979), the Okayama-Berg cloning system (Mol. Cell Biol. 2, 161–170, 1982), and the expression cloning vector recently described by Genetics Institute (Science 228, 810–815, 1985), are available which provide substantial assurance of at least some expression of conotoxin in the transformed eukaryotic cell line.

As previously mentioned, a convenient way to ensure production of a protein of the length of the conotoxins of interest is to produce the protein initially as a segment of a gene-encoded fusion protein. In such case, the DNA chain is constructed so that the expressed protein has enzymatic processing sites flanking the conotoxin amino acid residue sequences. A conotoxin-encoding DNA chain may be inserted, for example, into the beta-galactosidase gene for insertion into E. coli, in which case, the expressed fusion protein is subsequently cleaved with proteolytic enzymes to release the conotoxin from beta-galactosidase peptide sequences.

An advantage of inserting the protein-encoding sequence so that the desired sequence is expressed as a cleavable segment of a fusion protein, e.g. as the conotoxin sequence fused within the beta-galactosidase peptide sequence, is that the endogenous protein into which the desired conotoxin sequence is inserted is generally rendered non-functional, thereby facilitating selection for vectors encoding the fusion protein.

The conotoxin proteins may also be reproduced in yeast using known recombinant DNA techniques. For example, a suitable plasmid, amplified in an E. coli clone, is isolated and cleaved with Eco RI and Sal I. This digested plasmid is electrophoresed on an agarose gel allowing for the separation and recovery of the amplified insert of interest. The insert is inserted into the plasmic pYep, a shuttle vector which can be used to transform both E. coli and Saccharomyces cerevisiae yeast. Insertion of the synthetic DNA chain at this point assures that the DNA sequence is under the control of a promoter, in proper reading frame from an ATG signal and properly spaced relative to a cap site. The shuttle vector is used to transform URA3, a strain of S. cerevisiae yeast from which the oratate monophosphate decarboxylase gene is deleted.

The transformed yeast is grown in medium to attain log growth. The yeast is separated from its culture medium, and cell lysates are prepared. Pooled cell lysates are determined by RIA to be reactive with antibody raised against the conotoxin, demonstrating that a protein containing protein segment is expressed within the yeast cells.

The production of conotoxins can be carried out in both prokaryotic and eukaryotic cell lines to provide protein for biological and therapeutic use. While conotoxin synthesis is easily demonstrated using either bacteria or yeast cell lines, the synthetic genes should be insertable for expression in cells of higher animals, such as mammalian tumor cells, and in plants. Such mammalian cells may be grown, for example, as peritoneal tumors in host animals, and certain conotoxins may be harvested from the peritoneal fluid. The cloned DNA is insertable into plant varieties of interest where the plant utilizes it as a plant defense gene, i.e. it produces sufficient amounts of the pesticide of interest to ward off insects or the like that are natural predators to such plant species.

Although the above examples demonstrate that conotoxins can be synthesized through recombinant DNA techniques, the examples do not purport to have maximized conotoxin production. It is expected that subsequent selection of more efficient cloning vectors and host cell lines will increase the yield, and known gene amplification techniques for both eukaryotic and prokaryotic cells may be used to increase production. Secretion of the gene-encoded protein from the host cell line into the culture medium is also considered to be an important factor in obtaining certain of the synthetic proteins in large quantities.

Although the invention has been described with regard to certain preferred embodiments, it should be understood that various changes and modifications as would be obvious to one having the ordinary skill in the art may be made without departing from the scope of the invention which is set forth in appended claims. For example, substitution of various of the amino acid residues depicted in the amino acid sequences by residues known to be equivalent with those residues can be effected to produce equivalent peptides having similar biological activities. Moreover, it is known that additional substitutions in the amino acid sequence generally throughout the C-terminal portion of the peptide, i.e. within about ⅓ of the length of the conotoxin nearest its C-terminus, can be effected in order to produce conotoxins having phylogenetic specificity; thus, such substitutions in this region can be carried out to produce valuable equivalent structures. The C-terminus of many of the illustrated peptides is amidated, and the inclusion of a substituted amide at the C-terminus of such peptides, as described hereinbefore, is considered to create an equivalent conotoxin.

Particular features of the invention are emphasized in the claims which follow.

SEQUENCE LISTING

```
(1) GENERAL INFORMATION:

   (iii) NUMBER OF SEQUENCES: 13


(2) INFORMATION FOR SEQ ID NO: 1:

     (i) SEQUENCE CHARACTERISTICS:
          (A) LENGTH: 25 amino acids
          (B) TYPE: amino acid
          (D) TOPOLOGY: unknown

    (ii) MOLECULE TYPE: peptide

   (iii) HYPOTHETICAL: NO

    (iv) ANTI-SENSE: NO

    (xi) SEQUENCE DESCRIPTION: SEQ ID NO: 1:

Gly Cys Cys Gly Ser Tyr Pro Asn Ala Ala Cys His Pro Cys Ser Cys
1               5                   10                  15

Lys Asp Arg Xaa Ser Tyr Cys Gly Gln
            20                  25


(2) INFORMATION FOR SEQ ID NO: 2:

     (i) SEQUENCE CHARACTERISTICS:
          (A) LENGTH: 30 amino acids
          (B) TYPE: amino acid
          (D) TOPOLOGY: unknown

    (ii) MOLECULE TYPE: peptide

    (xi) SEQUENCE DESCRIPTION: SEQ ID NO: 2:

Glu Lys Ser Leu Val Pro Ser Val Ile Thr Thr Cys Cys Gly Tyr Asp
1               5                   10                  15

Xaa Gly Thr Met Cys Xaa Xaa Cys Arg Cys Thr Asn Ser Cys
            20                  25                  30


(2) INFORMATION FOR SEQ ID NO: 3:

     (i) SEQUENCE CHARACTERISTICS:
          (A) LENGTH: 19 amino acids
          (B) TYPE: amino acid
          (D) TOPOLOGY: unknown

    (ii) MOLECULE TYPE: peptide

    (xi) SEQUENCE DESCRIPTION: SEQ ID NO: 3:

Cys Cys Gly Val Xaa Asn Ala Ala Cys Pro Xaa Cys Val Cys Asn Lys
1               5                   10                  15

Thr Cys Gly
```

-continued (2) INFORMATION FOR SEQ ID NO: 4:

(i) SEQUENCE CHARACTERISTICS:
(A) LENGTH: 25 amino acids
(B) TYPE: amino acid
(D) TOPOLOGY: unknown (ii) MOLECULE TYPE: peptide (xi) SEQUENCE DESCRIPTION: SEQ ID NO: 4:

```
Gly Cys Cys Gly Ser Tyr Xaa Asn Ala Ala Cys His Xaa Cys Ser Cys
1               5                   10                  15

Lys Asp Arg Xaa Ser Tyr Cys Gly Gln
            20                  25
```

(2) INFORMATION FOR SEQ ID NO: 5:

(i) SEQUENCE CHARACTERISTICS:
(A) LENGTH: 25 amino acids
(B) TYPE: amino acid
(D) TOPOLOGY: unknown (ii) MOLECULE TYPE: peptide (xi) SEQUENCE DESCRIPTION: SEQ ID NO: 5:

```
Gly Cys Cys Gly Ser Tyr Xaa Asn Ala Ala Cys His Pro Cys Ser Cys
1               5                   10                  15

Lys Asp Arg Xaa Ser Tyr Cys Gly Gln
            20                  25
```

(2) INFORMATION FOR SEQ ID NO: 6:

(i) SEQUENCE CHARACTERISTICS:
(A) LENGTH: 18 amino acids
(B) TYPE: amino acid
(D) TOPOLOGY: unknown (ii) MOLECULE TYPE: peptide (xi) SEQUENCE DESCRIPTION: SEQ ID NO: 6:

```
Cys Cys Gly Val Xaa Asn Ala Ala Cys His Xaa Cys Val Cys Lys Asn
1               5                   10                  15

Thr Cys
```

(2) INFORMATION FOR SEQ ID NO: 7:

(i) SEQUENCE CHARACTERISTICS:
(A) LENGTH: 46 amino acids
(B) TYPE: amino acid
(D) TOPOLOGY: unknown (ii) MOLECULE TYPE: peptide (xi) SEQUENCE DESCRIPTION: SEQ ID NO: 7:

```
Gly Xaa Ser Phe Cys Lys Ala Asp Glu Lys Xaa Cys Glu Tyr His Ala
1               5                   10                  15

Asp Cys Cys Asn Cys Cys Leu Ser Gly Ile Cys Ala Xaa Ser Thr Asn
            20                  25                  30

Trp Ile Leu Pro Gly Cys Ser Thr Ser Ser Phe Phe Lys Ile
        35                  40                  45
```

(2) INFORMATION FOR SEQ ID NO: 8:

(i) SEQUENCE CHARACTERISTICS:
(A) LENGTH: 19 amino acids
(B) TYPE: amino acid

-continued (D) TOPOLOGY: unknown (ii) MOLECULE TYPE: peptide (xi) SEQUENCE DESCRIPTION: SEQ ID NO: 8:

```
Gly Cys Cys Ser His Pro Ala Cys Ser Gly Lys Tyr Gln Xaa Tyr Cys
1               5                   10                  15

Arg Xaa Ser
```

(2) INFORMATION FOR SEQ ID NO: 9:

(i) SEQUENCE CHARACTERISTICS:
(A) LENGTH: 23 amino acids
(B) TYPE: amino acid
(D) TOPOLOGY: unknown (ii) MOLECULE TYPE: peptide (xi) SEQUENCE DESCRIPTION: SEQ ID NO: 9:

```
His Xaa Xaa Cys Cys Leu Tyr Gly Lys Cys Arg Arg Tyr Xaa Gly Cys
1               5                   10                  15

Ser Ser Ala Ser Cys Cys Gln
            20
```

(2) INFORMATION FOR SEQ ID NO: 10:

(i) SEQUENCE CHARACTERISTICS:
(A) LENGTH: 27 amino acids
(B) TYPE: amino acid
(D) TOPOLOGY: unknown (ii) MOLECULE TYPE: peptide (xi) SEQUENCE DESCRIPTION: SEQ ID NO: 10:

```
Cys Lys Thr Tyr Ser Lys Tyr Cys Xaa Ala Asp Ser Xaa Cys Cys Thr
1               5                   10                  15

Xaa Gln Cys Val Arg Ser Tyr Cys Thr Leu Phe
            20                  25
```

(2) INFORMATION FOR SEQ ID NO: 11:

(i) SEQUENCE CHARACTERISTICS:
(A) LENGTH: 35 amino acids
(B) TYPE: amino acid
(D) TOPOLOGY: unknown (ii) MOLECULE TYPE: peptide (xi) SEQUENCE DESCRIPTION: SEQ ID NO: 11:

```
Ser Thr Ser Cys Met Glu Ala Gly Ser Tyr Cys Gly Ser Thr Thr Arg
1               5                   10                  15

Ile Cys Cys Gly Tyr Cys Ala Tyr Phe Gly Lys Lys Cys Ile Asp Tyr
            20                  25                  30

Pro Ser Asn
        35
```

(2) INFORMATION FOR SEQ ID NO: 12:

(i) SEQUENCE CHARACTERISTICS:
(A) LENGTH: 27 amino acids
(B) TYPE: amino acid
(D) TOPOLOGY: unknown (ii) MOLECULE TYPE: peptide (xi) SEQUENCE DESCRIPTION: SEQ ID NO: 12:

-continued

```
Gly Glu Xaa Xaa Val Ala Lys Met Ala Ala Xaa Leu Ala Arg Xaa Asn
1               5                   10                  15

Ile Ala Lys Gly Cys Lys Val Asn Cys Tyr Pro
            20                  25


(2) INFORMATION FOR SEQ ID NO: 13:

     (i) SEQUENCE CHARACTERISTICS:
          (A) LENGTH: 16 amino acids
          (B) TYPE: amino acid
          (D) TOPOLOGY: unknown

    (ii) MOLECULE TYPE: peptide

    (xi) SEQUENCE DESCRIPTION: SEQ ID NO: 13:

Glu Ser Glu Glu Gly Gly Ser Asn Ala Thr Lys Lys Pro Tyr Ile Leu
1               5                   10                  15
```

What is claimed is:

1. A substantially pure conotoxin which is highly selective for a specific human receptor, which conotoxin is selected from the group consisting of:

Gly-Xaa-Ser-Phe-Cys-Lys-Ala-Asp-Glu-Lys-Xaa-Cys-Glu-Tyr-His-Ala-Asp-Cys-Cys-Asn-Cys-Cys-Leu-Ser-Gly-Ile-Cys-Ala-Xaa-Ser-Thr-Asn-Trp-Ile-Leu-Pro-Gly-Cys-Ser-Thr-Ser-Ser-Phe-Phe-Lys-Ile (SEQ ID NO:7) wherein Xaa is 4Hyp;

Gly-Cys-Cys-Ser-His-Pro-Ala-Cys-Ser-Gly-Lys-Tyr-Gln-Xaa-Tyr-Cys-Arg-Xaa-Ser (SEQ ID NO:8) wherein Xaa is Gla and the C-terminus is amidated;

His-Xaa-Xaa-Cys-Cys-Leu-Tyr-Gly-Lys-Cys-Arg-Arg-Tyr-Xaa-Gly-Cys-Ser-Ser-Ala-Ser-Cys-Cys-Gln (SEQ ID NO:9) wherein Xaa is 4Hyp;

Cys-Lys-Thr-Tyr-Ser-Lys-Tyr-Cys-Xaa-Ala-Asp-Ser-Xaa-Cys-Cys-Thr-Xaa-Gln-Cys-Val-Arg-Ser-Tyr-Cys-Thr-Leu-Phe (SEQ ID NO:10) wherein Xaa is Gla and the C-terminus is amidated;

Ser-Thr-Ser-Cys-Met-Glu-Ala-Gly-Ser-Tyr-Cys-Gly-Ser-Thr-Thr-Arg-Ile-Cys-Cys-Gly-Tyr-Cys-Ala-Tyr-Phe-Gly-Lys-Lys-Cys-Ile-Asp-Tyr-Pro-Ser-Asn (SEQ ID NO:11);

Gly-Glu-Xaa-Xaa-Val-Ala-Lys-Met-Ala-Ala-Xaa-Leu-Ala-Arg-Xaa-Asn-Ile-Ala-Lys-Gly-Cys-Lys-Val-Asn-Cys-Tyr-Pro (SEQ ID NO:12) wherein Xaa is Gla; and Glu-Ser-Glu-Glu-Gly-Gly-Ser-Asn-Ala-Thr-Lys-Lys-Pro-Tyr-Ile-Leu (SEQ ID NO:13), wherein Glu in the 1-position is pGlu and the C-terminus is amidated.

2. A conotoxin according to claim 1 having the formula:

Gly-Xaa-Ser-Phe-Cys-Lys-Ala-Asp-Glu-Lys-Xaa-Cys-Glu-Tyr-His-Ala-Asp-Cys-Cys-Asn-Cys-Cys-Leu-Ser-Gly-Ile-Cys-Ala-Xaa-Ser-Thr-Asn-Trp-Ile-Leu-Pro-Gly-Cys-Ser-Thr-Ser-Ser-Phe-Phe-Lys-Ile (SEQ ID NO:7) wherein Xaa is 4Hyp.

3. A conotoxin according to claim 1 having the formula:

Gly-Cys-Cys-Ser-His-Pro-Ala-Cys-Ser-Gly-Lys-Tyr-Gln-Xaa-Tyr-Cys-Arg-Xaa-Ser (SEQ ID NO:8) wherein Xaa is Gla and the C-terminus is amidated.

4. A conotoxin according to claim 1 having the formula:

His-Xaa-Xaa-Cys-Cys-Leu-Tyr-Gly-Lys-Cys-Arg-Arg-Tyr-Xaa-Gly-Cys-Ser-Ser-Ala-Ser-Cys-Cys-Gln (SEQ ID NO:9) wherein Xaa is 4Hyp.

5. A conotoxin according to claim 1 having the formula:

Cys-Lys-Thr-Tyr-Ser-Lys-Tyr-Cys-Xaa-Ala-Asp-Ser-Xaa-Cys-Cys-Thr-Xaa-Gln-Cys-Val-Arg-Ser-Tyr-Cys-Thr-Leu-Phe (SEQ ID NO:10) wherein Xaa is Gla and the C-terminus is amidated.

6. A conotoxin according to claim 1 having the formula:

Ser-Thr-Ser-Cys-Met-Glu-Ala-Gly-Ser-Tyr-Cys-Gly-Ser-Thr-Thr-Arg-Ile-Cys-Cys-Gly-Tyr-Cys-Ala-Tyr-Phe-Gly-Lys-Lys-Cys-Ile-Asp-Tyr-Pro-Ser-Asn (SEQ ID NO:11).

7. A conotoxin according to claim 1 having the formula:

Gly-Glu-Xaa-Xaa-Val-Ala-Lys-Met-Ala-Ala-Xaa-Leu-Ala-Arg-Xaa-Asn-Ile-Ala-Lys-Gly-Cys-Lys-Val-Asn-Cys-Tyr-Pro (SEQ ID NO:12) wherein Xaa is Gla.

8. A conotoxin according to claim 1 having the formula:

Glu-Ser-Glu-Glu-Gly-Gly-Ser-Asn-Ala-Thr-Lys-Lys-Pro-Tyr-Ile-Leu (SEQ ID NO:13), wherein Glu in the 1-position is pGlu and the C-terminus is amidated.

*9. The conotoxin according to claim 8 wherein the Thr residue is glycosylated.*

*10. A substantially pure conotoxin having the amino acid sequence Glu-Ser-Glu-Glu-Gly-Gly-Ser-Asn-Ala-Thr-Lys-Lys-Pro-Tyr-Ile-Leu (SEQ ID NO:13), wherein Glu in the 1-position is pGlu.*

*11. The substantially pure conotoxin of claim 10, wherein the Thr residue is glycosylated.*

*12. An isolated conotoxin which is highly selective for a specific human receptor, comprising a conotoxin selected from the group consisting of:*

*Gly-Xaa-Ser-Phe-Cys-Lys-Ala-Asp-Glu-Lys-Xaa-Cys-Glu-Tyr-His-Ala-Asp-Cys-Cys-Asn-Cys-Cys-Leu-Ser-Gly-Ile-Cys-Ala-Xaa-Ser-Thr-Asn-Trp-Ile-Leu-Pro-Gly-Cys-Ser-Thr-Ser-Ser-Phe-Phe-Lys-Ile (SEQ ID NO:7) wherein Xaa is 4Hyp;*

*Gly-Cys-Cys-Ser-His-Pro-Ala-Cys-Ser-Gly-Lys-Tyr-Gln-Xaa-Tyr-Cys-Arg-Xaa-Ser (SEQ ID NO:8) wherein Xaa is Gla and the C-terminus is amidated;*

*His-Xaa-Xaa-Cys-Cys-Leu-Tyr-Gly-Lys-Cys-Arg-Arg-Tyr-Xaa-Gly-Cys-Ser-Ser-Ala-Ser-Cys-Cys-Gln (SEQ ID NO:9) wherein Xaa is 4Hyp;*

*Cys-Lys-Thr-Tyr-Ser-Lys-Tyr-Cys-Xaa-Ala-Asp-Ser-Xaa-Cys-Cys-Thr-Xaa-Gln-Cys-Val-Arg-Ser-Tyr-Cys-Thr-Leu-Phe (SEQ ID NO:10) wherein Xaa is Gla and the C-terminus is amidated;*

*Ser-Thr-Ser-Cys-Met-Glu-Ala-Gly-Ser-Tyr-Cys-Gly-Ser-Thr-Thr-Arg-Ile-Cys-Cys-Gly-Tyr-Cys-Ala-Tyr-Phe-Gly-Lys-Lys-Cys-Ile-Asp-Tyr-Pro-Ser-Asn* (*SEQ ID NO:11*);

*Gly-Glu-Xaa-Xaa-Val-Ala-Lys-Met-Ala-Ala-Xaa-Leu-Ala-Arg-Xaa-Asn-Ile-Ala-Lys-Gly-Cys-Lys-Val-Asn-Cys-Tyr-Pro* (*SEQ ID NO:12*) *wherein Xaa is Gla; and*

*Glu-Ser-Glu-Glu-Gly-Gly-Ser-Asn-Ala-Thr-Lys-Lys-Pro-Tyr-Ile-Leu* (*SEQ ID NO:13*), *wherein Glu in the 1-position is pGlu and the C-terminus is amidated.*

*13. The conotoxin according to claim 12 comprising the formula:*

*Gly-Xaa-Ser-Phe-Cys-Lys-Ala-Asp-Glu-Lys-Xaa-Cys-Glu-Tyr-His-Ala-Asp-Cys-Cys-Asn-Cys-Cys-Leu-Ser-Gly-Ile-Cys-Ala-Xaa-Ser-Thr-Asn-Trp-Ile-Leu-Pro-Gly-Cys-Ser-Thr-Ser-Ser-Phe-Phe-Lys-Ile* (*SEQ ID NO:7*) *wherein Xaa is 4Hyp.*

*14. The isolated conotoxin according to claim 12 comprising the formula:*

*Gly-Cys-Cys-Ser-His-Pro-Ala-Cys-Ser-Gly-Lys-Tyr-Gln-Xaa-Tyr-Cys-Arg-Xaa-Ser* (*SEQ ID NO:8*) *wherein Xaa is Gla and the C-terminus is amidated.*

*15. The isolated conotoxin according to claim 12 comprising the formula:*

*His-Xaa-Xaa-Cys-Cys-Leu-Tyr-Gly-Lys-Cys-Arg-Arg-Tyr-Xaa-Gly-Cys-Ser-Ser-Ala-Ser-Cys-Cys-Gln* (*SEQ ID NO:9*) *wherein Xaa is 4Hyp.*

*16. The isolated conotoxin according to claim 12 comprising the formula:*

*Cys-Lys-Thr-Tyr-Ser-Lys-Tyr-Cys-Xaa-Ala-Asp-Ser-Xaa-Cys-Cys-Thr-Xaa-Gln-Cys-Val-Arg-Ser-Tyr-Cys-Thr-Leu-Phe* (*SEQ ID NO:10*) *wherein Xaa is Gla and the C-terminus is amidated.*

*17. The isolated conotoxin according to claim 12 comprising the formula:*

*Ser-Thr-Ser-Cys-Met-Glu-Ala-Gly-Ser-Tyr-Cys-Gly-Ser-Thr-Thr-Arg-Ile-Cys-Cys-Gly-Tyr-Cys-Ala-Tyr-Phe-Gly-Lys-Lys-Cys-Ile-Asp-Tyr-Pro-Ser-Asn* (*SEQ ID NO:11*).

*18. The isolated conotoxin according to claim 12 comprising the formula:*

*Gly-Glu-Xaa-Xaa-Val-Ala-Lys-Met-Ala-Ala-Xaa-Leu-Ala-Arg-Xaa-Asn-Ile-Ala-Lys-Gly-Cys-Lys-Val-Asn-Cys-Tyr-Pro* (*SEQ ID NO:12*) *wherein Xaa is Gla.*

*19. The isolated conotoxin according to claim 12 comprising the formula:*

*Glu-Ser-Glu-Glu-Gly-Gly-Ser-Asn-Ala-Thr-Lys-Lys-Pro-Tyr-Ile-Leu* (*SEQ ID NO:13*), *wherein Glu in the 1-position is pGlu and the C-terminus is amidated.*

*20. The isolated conotoxin according to claim 19 wherein the Thr residue is glycosylated.*

*21. An isolated conotoxin comprising the amino acid sequence Glu-Ser-Glu-Glu-Gly-Gly-Ser-Asn-Ala-Thr-Lys-Lys-Pro-Tyr-Ile-Leu* (*SEQ ID NO:13*), *wherein Glu in the 1-position is pGlu.*

*22. An isolated conotoxin comprising the amino acid sequence Glu-Ser-Glu-Glu-Gly-Gly-Ser-Asn-Ala-Thr-Lys-Lys-Pro-Tyr-Ile-Leu* (*SEQ ID NO:13*), *wherein Glu in the 1-position is pGlu and the Thr residue is glycosylated.*

* * * * *